United States Patent
Schnorrenberg et al.

[11] Patent Number: 6,124,296
[45] Date of Patent: *Sep. 26, 2000

[54] ARYLGLYCINAMIDE DERIVATIVES, METHODS OF PRODUCING THESE SUBSTANCES AND PHARMACEUTICAL COMPOSITIONS CONTAINING SUCH COMPOUNDS

[75] Inventors: Gerd Schnorrenberg, Gau-Algesheim; Horst Dollinger; Franz Esser, both of Ingelheim am Rhein; Hans Briem, Budenheim; Birgit Jung, Bingen; Georg Speck, Ingelheim am Rhein, all of Germany

[73] Assignee: Boehringer Ingelheim KG, Ingelheim am Rhein, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/930,704

[22] PCT Filed: Apr. 11, 1996

[86] PCT No.: PCT/EP96/01548

§ 371 Date: Oct. 29, 1997

§ 102(e) Date: Oct. 29, 1997

[87] PCT Pub. No.: WO96/32386

PCT Pub. Date: Oct. 17, 1996

[30] Foreign Application Priority Data

Apr. 14, 1995 [DE] Germany .......................... 195 14 112
May 25, 1995 [DE] Germany .......................... 195 19 245

[51] Int. Cl.$^7$ .................. A61K 31/495; C07D 295/15
[52] U.S. Cl. .............................. 514/255; 544/400
[58] Field of Search ............... 544/400; 514/255

[56] References Cited

U.S. PATENT DOCUMENTS 3,518,274 6/1970 Strycker .
3,862,946 1/1975 Havera .
3,906,100 9/1975 Havera .
5,710,155 1/1998 Schnorrenberg et al. .

FOREIGN PATENT DOCUMENTS

WO 94/01402 1/1994 WIPO .
WO 94/10146 5/1994 WIPO .
WO 95/26335 10/1995 WIPO .
WO 96/08480 3/1996 WIPO .

OTHER PUBLICATIONS

Shah, K.J. and Trivedi, J.J., "Potential Local Anesthetics. V. Synthesis of Basic N–(Substituted Benzyl)Phenylacetamides," *Chem. Abstr.* 68:5715. Abstract No. 59230g (1968).

Nagarajan, K. et al., "A Novel Displacement Reaction On α–Chlorodiphenylacetamides," *Tetrahedron Letts.* 15:1387–1390 (1967).

Patel, B.M. et al., "Evaluation of New Series of Lignocaine Analogs," *Chem. Abstr.* 76:7. Abstract No. 54228t (1972).

Patel, B.M., et al., "Evaluation of New Series of Lignocaine Analogues," *Indian J. Pharm.* 33:86–89 (1971).

Shah, K.J. and Trivedi, J.J., "Potential Local Anaesthetics. Part V. Synthesis of Basic N–(Substituted benzyl) Phenyl Acetamides," *Indian J. Appl. Chem.* 30:11–13 (1967).

An English–language version of the International Search Report for corresponding International Application No. PCT/EP96/01548.

*Primary Examiner*—Robert W. Ramsuer
*Attorney, Agent, or Firm*—Sterne, Kessler, Goldstein & Fox P.L.L.C.

[57] ABSTRACT

The invention relates to new arylglycinamide derivatives of general formula I

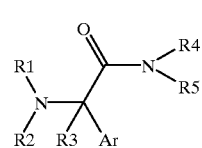

and the pharmaceutically acceptable salts thereof, wherein $R^1$ and $R^2$ together with the N to which they are bound form a ring of the formula

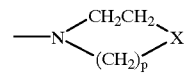

wherein
p is 2 or 3 and
X denotes oxygen, $N(CH_2)_n R^6$ or $CR^7 R^8$,
and $R^3, R^4, R^5, R^6, R^7, R^8$, Ar and n have the meanings given in the specification, and the preparation and use thereof. The new compounds are valuable neurokinin (tachykinin)-antagonists.

22 Claims, No Drawings

ARYLGLYCINAMIDE DERIVATIVES, METHODS OF PRODUCING THESE SUBSTANCES AND PHARMACEUTICAL COMPOSITIONS CONTAINING SUCH COMPOUNDS

This application is a 371 of PCT/EP96/01548 filed Apr. 11, 1996.

SUMMARY OF THE INVENTION

The invention relates to new arylglycinamide derivatives of general formula I

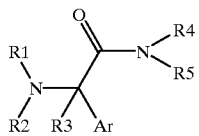

and the pharmaceutically acceptable salts thereof, processes for preparing them and pharmaceutical compositions containing these compounds. The compounds are valuable neurokinin (tachykinin) antagonists.

DETAILED DESCRIPTION OF THE INVENTION

The abbreviations used in the specification and claims are explained as follows:

| | |
|---|---|
| CDI | = Carbonyldiimidazole |
| DCCI | = Dicyclohexylcarbodiimide |
| HOBt | = 1-Hydroxybenzotriazole |
| THF | = Tetrahydrofuran |
| DMF | = Dimethylformamide |
| RT | = Room temperature |
| DMAP | = 4-Ditmethylaminopyridine |
| TBTU | = O-Benzotriazolyl-tetramethyluronium-tetrafluoroborate |

In order to show the formulae, a simplified representation is used. In the representation of the compounds all CH$_3$— substituents are represented by a single bond, and for example the following formula

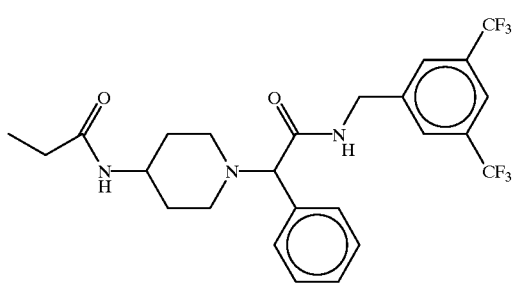

represents

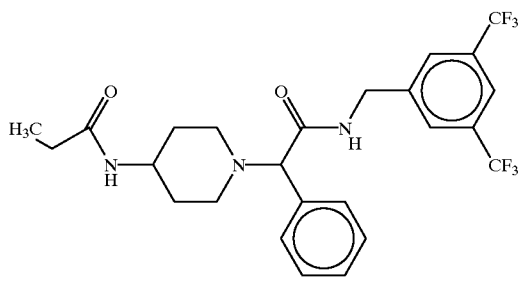

The invention relates to new arylglycinamide derivatives of general formula I

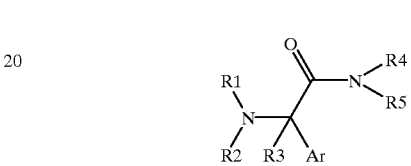

or the pharmaceutically acceptable salts thereof, wherein

Ar denotes unsubstituted or mono- to penta-substituted phenyl, or unsubstituted or mono- or di-substituted naphthyl, [in which the substituents of the phenyl and naphthyl independently of each other denote halogen (F, Cl, Br, I), OH, (C$_{1-4}$)alkyl, O—(C$_{1-4}$) alkyl, CF$_3$, OCF$_3$ or NR$^9$R$^{10}$ (wherein R$^9$ and R$^{10}$ independently of each other denote H, methyl or acetyl)] or Ar is phenyl substituted by —OCH$_2$O— or —O(CH$_2$)$_2$O—;

R$^1$ and R$^2$ together with the N to which they are bound form a ring of the formula

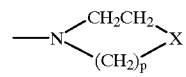

wherein p is 2 or 3,

X denotes oxygen, N(CH$_2$)$_n$R$^6$ or CR$^7$R$^8$, wherein n is 0, 1 or 2,

R$^6$ is (C$_{3-7}$)cycloalkyl, phenyl or naphthyl, wherein the phenyl may be mono- to tri-substituted by halogen (F, Cl, Br, I) , (C$_{1-4}$) alkyl, O—(C$_{1-4}$)alkyl, CF$_3$, OCF$_3$ or NR$^{15}$R$^{16}$ (wherein R$^{15}$ and R$^{16}$ independently of each other denote H, methyl or acetyl);

R$^7$ and R$^8$ have one of the following meanings:
 a) R$^7$ and R$^8$ represent H if R$^3$ is unsubstituted or substituted phenyl,
 b) R$^7$ is phenyl, phenyl substituted by 1 to 3 substituents [wherein the substituents independently of one another denote halogen (F, Cl, Br, I), (C$_{1-4}$)alkyl, O—(C$_{1-4}$) alkyl, CF$_3$ or OCF$_3$], piperidinyl, 1-methylpiperidinyl,

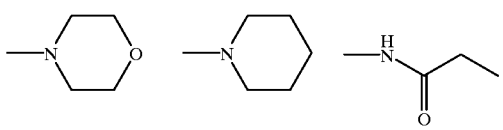

-continued

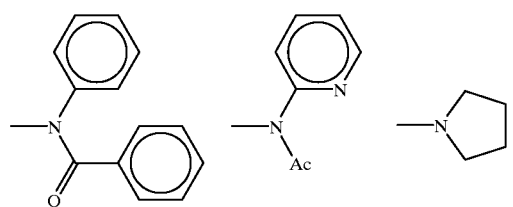

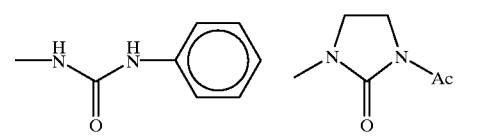

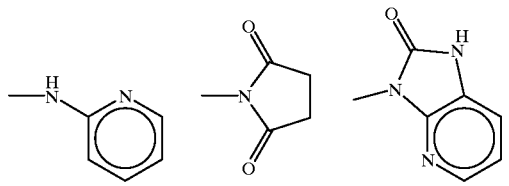

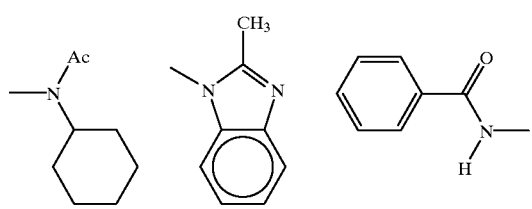

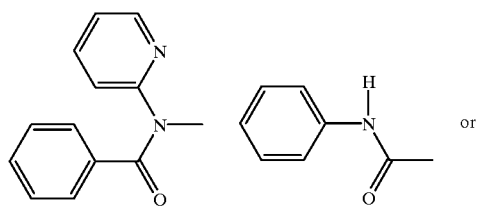

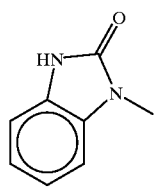

if R⁸ is H, —CONH₂, —NHC(O)CH₃, —N(CH₃)C(O)CH₃, CN

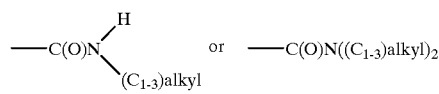

or c) R⁷ and R⁸ together form the group

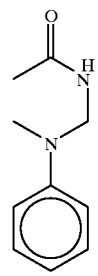

R³ denotes H, (C₁₋₄)alkyl, unsubstituted or mono- to tri-substituted phenyl, wherein the substituents independently of one another represent halogen (F, Cl, Br, I), (C₁₋₄)alkyl, O—(C₁₋₄)alkyl, CF₃, OCF₃ or NR¹⁷R¹⁸ (wherein R¹⁷ and R¹⁸ independently of one another denote H, methyl or acetyl);

R⁴ denotes phenyl(C₁₋₄)alkyl or naphthyl(C₁₋₄)alkyl, wherein phenyl may be substituted by 1 to 3 substituents, wherein the substituents independently of one another are halogen (F, Cl, Br, I), (C₁₋₄)alkyl, O—(C₁₋₄)alkyl, CF₃, OCF₃ or NR¹⁹R²⁰ (wherein R¹⁹ and R²⁰ independently of one another denote H, methyl or acetyl); and R⁵ denotes H, (C₁₋₄)alkyl, (C₃₋₆)cycloalkyl, CH₂COOH, —CH₂C(O)NH₂, —OH or phenyl(C₁₋₄)alkyl.

The compounds according to the invention are valuable neurokinin (tachykinin) antagonists which have both substance P-antagonism and also neurokinin A- or neurokinin B-antagonistic properties. They are useful for the treatment and prevention of neurokinin-mediated diseases.

Compounds of general formula I may contain acid groups, chiefly carboxyl groups, and/or basic groups such as, for example, amino functions. Compounds of general formula I may therefore be obtained either as internal salts, as salts with pharmaceutically acceptable inorganic acids such as hydrochloric acid, sulphuric acid, phosphoric acid or sulphonic acid or organic acids (such as, for example, maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as, for example, diethylamine, triethylamine or triethanolamine, etc.

The compounds according to the invention may occur as racemates but may also be obtained as pure enantiomers, i.e. in (R) or (S)-form. They may also occur as diastereoisomers or mixtures thereof.

The preferred compounds of general formula I are those wherein

R¹ and R² together with the N to which they are bound form a 6-membered ring of the formula

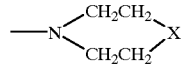

wherein

X denotes N(CH₂)ₙR⁶ or CR⁷R⁸, wherein n, $R^6$, $R^7$ and $R^8$ are defined as in claim 1.

Particular mention should be made of compounds of formula I wherein

X is $N(CH_2)_nR^6$ wherein n is 0, 1 or 2 and $R^6$ is $(C_{3-7})$ cycloalkyl or phenyl, particularly those compounds wherein n is O and $R^6$ is $(C_{3-7})$cycloalkyl, particularly those compounds wherein $R^6$ is cyclobutyl or cyclohexyl.

Mention should also be made of compounds of formula I wherein $R^7$ and $R^8$ have one of the following meanings:

a) $R^7$ and $R^8$ denote H when $R^3$ is unsubstituted or substituted phenyl, b) $R^7$ is phenyl, piperidinyl

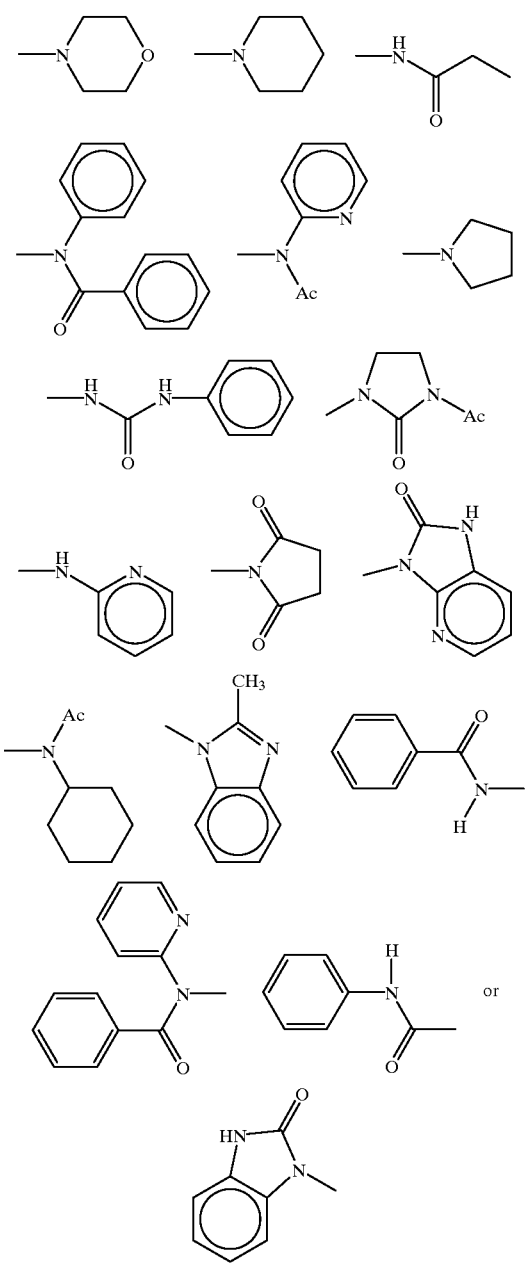

if $R^8$ is H, $-CONH_2$, $-NHC(O)CH_3$, $-N(CH_3)C(O)CH_3$ or CN, or c) $R^7$ and $R^8$ together form the group

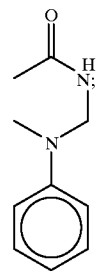

particularly those wherein $R^7$ and $R^8$ have one of the following meanings:

a) $R^7$ and $R^8$ denote H when $R^3$ is unsubstituted or substituted phenyl, b) $R^7$ is phenyl,

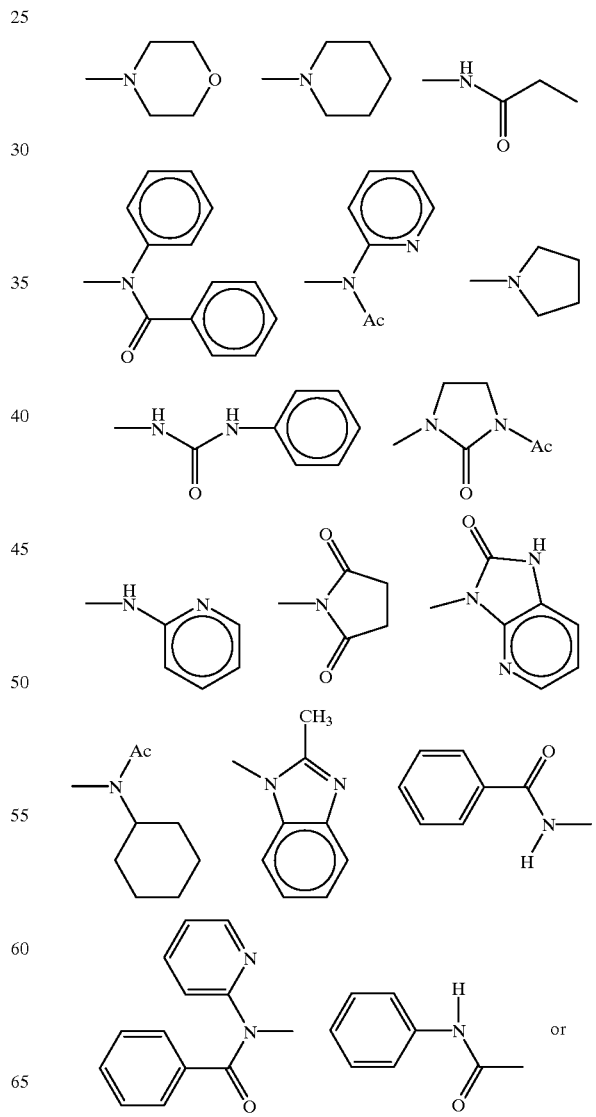

-continued

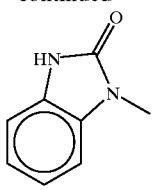

when R⁸ is H, —CONH₂ or CN, or
c) R⁷ and R⁸ together form the group

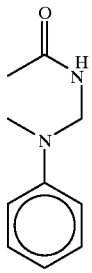

The preferred compounds are those wherein R⁷ denotes phenyl,

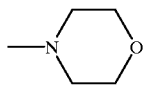  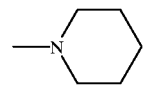

or 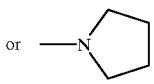

and R⁸ is H or CN, particularly those wherein R⁷ is pyridino and R⁸ is H.

Of the compounds defined above, the preferred ones are those wherein

Ar denotes unsubstituted or mono- or di-substituted phenyl, or unsubstituted naphthyl [wherein the substituents of the phenyl independently of one another are halogen (F, Cl, Br, I), OH, methyl, methoxy, CF₃, OCF₃ or dimethylamine] or Ar is phenyl substituted by —OCH₂O—, this group connecting positions 2 and 3 or 3 and 4 of the phenyl, particularly those wherein Ar denotes unsubstituted or mono- or di-substituted phenyl, or unsubstituted naphthyl [wherein the substituents of the phenyl independently of one another are halogen (F, Cl, Br), methoxy or CF₃] or Ar is phenyl substituted by —OCH₂O—, this group connecting positions 2 and 3 or 3 and 4 of the phenyl.

The preferred compounds are those wherein Ar is phenyl, 3,4-dichlorophenyl, 3,4-dimethoxyphenyl or 3,4-methylenedioxyphenyl.

Of the compounds defined above, particular mention should be made of those wherein R³ is phenyl or preferably H.

Of the compounds defined above, mention should also be made of those wherein

R⁴ denotes phenyl(C₁₋₃)alkyl, wherein phenyl may be substituted by 1 or 2 substituents, the substituents independently of one another being halogen (F, Cl, Br, I), methyl, methoxy, CF₃ or OCF₃; and R⁵ denotes H, (C₁₋₃)alkyl, CH₂COOH, —CH₂C(O)NH₂ or phenethyl, particularly those compounds wherein
R⁴ is

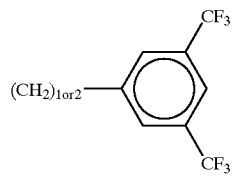

and R⁵ denotes H or CH₃.

The following compounds are preferred:

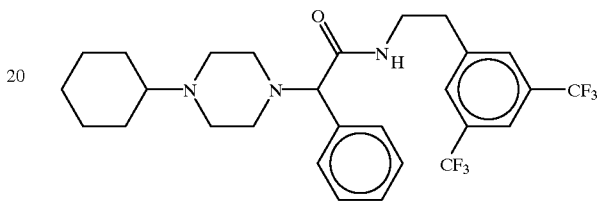

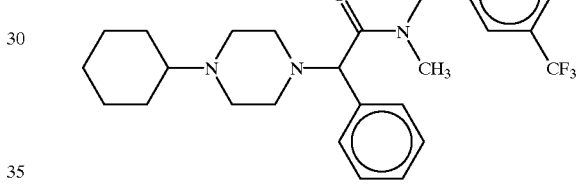

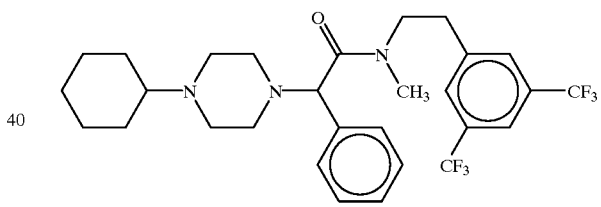

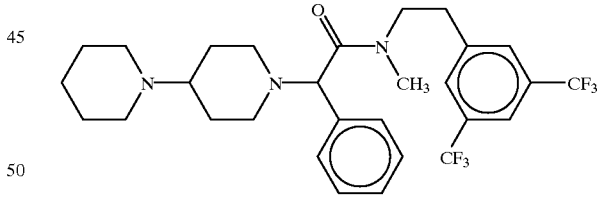

and

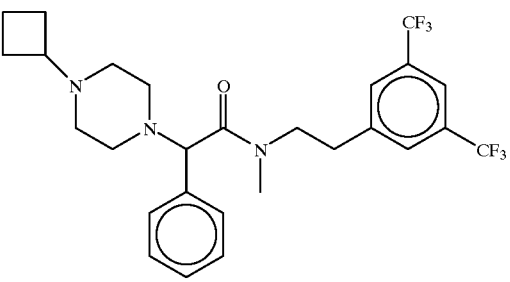

The term naphthyl used above includes both 1-naphthyl and 2-naphthyl.

Test results for compounds according to the invention:

The receptor affinity for the $NK_1$-receptor (substance P-receptor) is determined on human lymphoblastoma cells (IM-9) with cloned $NK_1$-receptors, measuring the displacement of $^{125}I$-labelled substance P. The $K_i$-values thus obtained demonstrate the efficacy of the compounds:

|  | $K_i$ |
|---|---|
| Compound of Example 3: | 1.4 nM |
| Compound of Example 4: | 1.0 nM |
| Compound of Example 5: | 1.3 nM |
| Compound of Example 33: | 1.3 nM |
| Compound of Example 45: | 1.6 nM |
| Compound of Example 46: | 1.4 nM |
| Compound of Example 52: | 1.1 nM |
| Compound of Example 53: | 2.3 nM |
| Compound of Example 58: | 6.4 nM |
| Compound of Example 59: | 4.2 nM |
| Compound of Example 65: | 9.2 nM |
| Compound of Example 66: | 1.4 nM |
| Compound of Example 68: | 1.5 nM |
| Compound of Example 70: | 2.8 nM |
| Compound of Example 71: | 2.1 nM |
| Compound of Example 72: | 6.8 nM |
| Compound of Example 73: | 1.7 nM |
| Compound of Example 74: | 11.8 nM |
| Compound of Example 75: | 180 nM |
| Compound of Example 76: | 7.0 nM |

The compounds according to the invention are valuable neurokinin (tachykinin) antagonists which have, in particular, $NK_1$-antagonism, but also $NK_2$- and $NK_3$-antagonistic properties.

The compounds according to the invention are valuable neurokinin (tachykinin) antagonists which have both substance P-antagonism and also neurokinin A- or neurokinin B-antagonistic properties. They are useful for the treatment and prevention of neurokinin-mediated diseases: treatment and prevention of inflammatory and allergic diseases of the respiratory tract, such as asthma, chronic bronchitis, emphysema, rhinitis or coughs, eye diseases such as conjunctivitis and iritis, skin diseases such as dermatitis in contact eczema, urticaria, psoriasis, sunburn, insect bites and stings, neurodermitis, itching and postherpetic pain, diseases of the gastrointestinal tract such as gastric and duodenal ulcers, ulcerative colitis, Crohn's disease, irritable bowel, Hirschsprung's disease;

diseases of the joints such as rheumatoid arthritis, reactive arthritis and Reiter syndrome;

for treating diseases of the central nervous system such as dementia, Alzheimer's disease, schizophrenia, psychosis, depression, headaches (e.g. migraine or tension headaches) and epilepsy;

for the treatment of tumours, collagenosis, dysfunction of the urinary tract, haemorrhoids, nausea and vomiting, triggered for example by radiation or cytostatic therapy or motion and pain of all kinds.

The invention therefore also relates to the use of the compounds according to the invention as remedies and pharmaceutical preparations which contain these compounds. They are preferably for use in humans. The compounds according to the invention may be administered by intravenous, subcutaneous, intramuscular, intraperitoneal or intranasal route or by inhalation, by transdermal route, if desired with the aid of iontophoresis or enhancers known from the literature, and by oral route.

For parenteral administration, the compounds of formula I or the physiologically acceptable salts thereof, optionally with conventional substances such as solubilisers, emulsifiers or other adjuvants, may be made into solutions, suspensions or emulsions. Suitable solvents include, for example, water, physiological saline solutions or alcohols, e.g. ethanol, propanediol or glycerol, sugar solutions such as glucose or mannitol solutions or a mixture of various solvents.

In addition, the compounds may be administered by means of implants, e.g. of polylactide, polyglycolide or polyhydroxybutyric acid or by means of intranasal preparations.

The oral effectiveness of compounds of general formula I can be demonstrated using the following standard test:

Inhibition of the lowering of blood pressure caused by $NK_1$ in anaesthetised guinea pigs.

Guinea pigs weighing 300–500 grams were anaesthetised with pentobarbital (50 mg/kg i.p.), intubated and mechanically ventilated with 10 ml of ambient air per kg of body weight at a rate of 60 breaths per minute. The blood pressure was measured in the blood flow through the carotid artery. In order to introduce substances intravenously, the jugular vein was cannulated.

By the intravenous administration of the $NK_1$-agonist [$\beta Ala^4$, $Sar^9$, $Met(O_2)^{11}$] SP(4–11) (0.2 $\mu$mol/kg) a brief lowering of the blood pressure was triggered which was repeated at 10 minute intervals by repeatedly giving the $NK_1$-agonist.

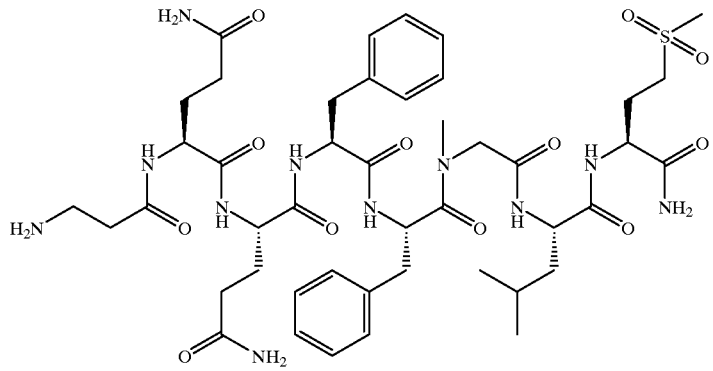

The neurokinin-antagonist was then administered by intraduodenal route and at 10 minute intervals a lowering of blood pressure was induced by means of the $NK_1$-agonist.

EXAMPLES

The inhibition of the lowering of blood pressure caused by the above-mentioned $NK_1$-agonist was measured before and after treatment with the neurokinin-antagonist.

The compound of Example 5 yielded an $ID_{50}$ of 1.4 mg/kg. ($ID_{50}$ is the dose which inhibits the lowering of blood pressure caused by the $NK_1$-agonist by 50%.)

The compounds according to the invention may be prepared by generally known methods.

The compounds may be prepared in various ways. The two commonest methods are shown in the following scheme:

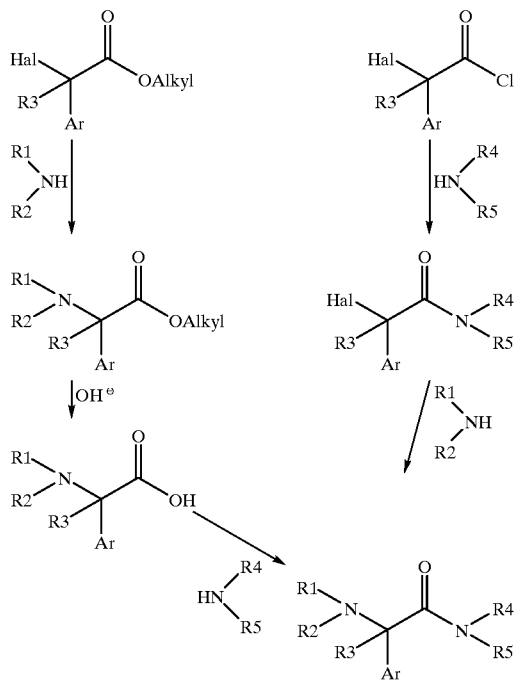

Method A. The carboxylic acid may be linked to the amine $HN(R^5)R^4$ in various ways. The usual methods are coupling methods such as those used in peptide chemistry. A coupling reagent such as TBTU, DCCI/HOBt, CDI, etc., is added to the coupling partners in an approximately equivalent amount. Suitable solvents are DMF, THF, $CH_2Cl_2$, $CHCl_3$, acetonitrile or other inert solvents or mixtures thereof. The appropriate temperature range is between −50° C. and +120° C., preferably between 0° C. and 40° C.

The carboxylic acid may also initially be converted by means of $SOCl_2$, $SO_2Cl_2$, $PCl_3$, $PCl_5$ or $PBr_3$ or mixtures thereof, by known methods, into the corresponding acid halide which is subsequently reacted with the amine $HN(R^5)R^4$ in an inert solvent such as $CH_2Cl_2$, THF or dioxane at temperatures between −50° C. and +100° C., typically between 0° C. and 20° C.

Another alternative is to convert the carboxylic acid initially into the alkylester, usually the methylester, by known methods and then to react this ester with the amine $HN(R^5)R^4$ in an inert solvent such as DMF, dioxane or THF. The reaction temperatures are between 20° C. and 150° C., typically between 50° C. and 120° C. The reaction may also be carried out in a pressurised container.

Process B. In this, the α-halo-arylacetamide derivative obtained according to known procedures is reacted with the amine $R^1(R^2)NH$, thereby generating hydrogen halide. In order to mop up the cleaved (or excess) hydrogen halide, inorganic bases are used such as $K_2CO_3$, $NaHCO_3$ or $CaCO_3$, or organic bases may be used such as triethylamine, Hünig base, pyridine or DMAP, or an excess of the amine $R^1(R^2)NH$ may be used. DMF, THF, dioxane or other inert solvents are used. The temperature range for the reaction is from 0 to 100° C., typically from 10 to 80° C.

Process C. The compounds according to the invention in which $R^5$ is not H may also be prepared as follows: first of all, the corresponding compound in which $R^5$ is H is synthesised according to process A or B. Then N-alkylation is carried out as follows in order to introduce alkyl, cycloalkyl or $CH_2COOH$. The compound according to the invention wherein $R^5$ is H is deprotonated with an equivalent quantity of NaH, $NaNH_2$, KOH, $NaOCH_3$ or some other strong base. Anhydrous inert solvents such as THF, dioxane or diethylether are used. Then the corresponding alkylating agent is added slowly in the form of the corresponding halide, tosylate or mesylate. The reaction is carried out in the temperature range from −50° C. to +100° C., typically between 0° C. and +50° C. The method is described in detail in Example 33.

Example 1

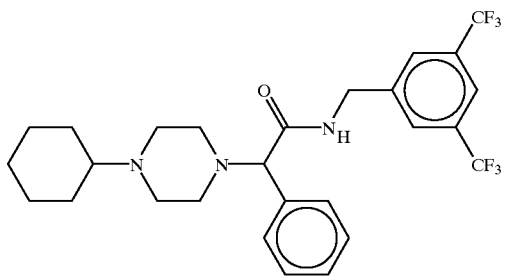

1st Step: 2.2 g of 1-cyclohexylpiperazine were dissolved in 150 ml of anhydrous DMF, mixed with 2 g of $K_2CO_3$, stirred at room temperature for 20 minutes and then cooled to 5° C. 2.7 g of methyl (R,S)-α-bromophenylacetic acid were added and the suspension was stirred overnight at RT. The precipitate was filtered off and the filtrate was evaporated down. The residue was taken up in ethyl acetate, extracted twice with 10% $KHCO_3$ solution and once with saturated NaCl solution. The organic phase was dried over $Na_2SO_4$, filtered and evaporated down, and 3.7 g of (R,S)-1-cyclohexyl-4-(methyl 2-phenylacetate)-piperazine were obtained in the form of a yellow oil.

Yield: about 100%.

2nd Step: 2.3 g of the product of the first step were dissolved in 10 ml of methanol, mixed with 14 ml of 1N NaOH and the resulting emulsion was stirred overnight at room temperature. The clear reaction solution was neutralised by the addition of 14 ml of 1N HCl, evaporated to dryness, the residue was treated with isopropanol and the solid matter was collected by suction filtration. The filtrate was evaporated down and the residue was triturated again with isopropanol, the solid matter was suction filtered and combined with the solid obtained earlier. In this way, 1.6 g of (R,S)-1-cyclohexyl-4-(2-phenylacetic acid)-piperazine were obtained as a white solid.

Yield: 75%.

3rd Step: 0.6 g of the product of the second step, 0.48 g of 3,5-bis-(trifluoromethyl)-benzylamine and 0.32 g of HOBT were suspended in 60 ml of THF/CH$_2$Cl$_2$ (1:1) and adjusted to pH 8.5 by the addition of about 0.7 ml of Hünig base. 0.77 g of TBTU were added and the mixture was stirred overnight at room temperature. The clear reaction solution was evaporated down in vacuo, the residue was taken up in CH$_2$Cl$_2$ and extracted twice with 10% KHSO$_4$ solution, once with saturated NaCl solution, twice with 10% KHCO$_3$ solution and once more with saturated NaCl solution. The organic phase was dried over Na$_2$SO$_4$, filtered and evaporated down, whereupon crystallisation took place. 0.685 g of (R,S)-1-cyclohexyl-piperazinyl-4-[2-phenylacetic acid-N-(3,5-bis-trifluoromethylbenzyl)amide] were obtained as a yellowish solid.

Yield 64%. Mp: 124–129° C. FAB-MS: (M+H)$^+$=528.2.

Example 2

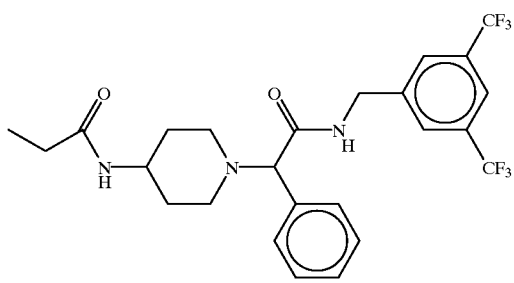

1st Step: 0.49 g of 3,5-bis-(trifluoromethyl)-benzylamine were dissolved in 30 ml of anhydrous CH$_2$Cl$_2$, 0.3 ml of triethylamine were added, the mixture was cooled in an ice bath and over 20 minutes a solution of 0.46 g of (R,S)-α-bromophenylacetyl chloride in 10 ml of CH$_2$Cl$_2$ was added dropwise. After the mixture had stood at room temperature over a weekend, the solvent was eliminated and the solid residue was triturated with diethylether, suction filtered and the filtrate was evaporated down. 0.6 g of α-bromophenylacetic acid N-(bis-trifluoromethyl-benzyl)-amide were obtained as a light beige solid.

Yield: 43.5%.

2nd Step: 0.21 g of 4-propionylamino-piperidine hydrochloride were dissolved in 30 ml of anhydrous DMF, 0.33 g of K$_2$CO$_3$ were added and the mixture was stirred for 30 minutes at room temperature. Over 20 minutes a solution of 0.68 g of the product of the first step in 10 ml of DMF were added dropwise to this mixture, which was then stirred overnight at room temperature. The suspension was filtered, the filtrate was evaporated down, the oily residue obtained was taken up in ethyl acetate, extracted twice with 10% KHCO$_3$ solution and once with saturated NaCl solution. The organic phase was dried over Na$_2$SO$_4$, filtered, the filtrate was evaporated down and the semi-solid residue obtained was triturated with diethylether and suction filtered. 0.33 g of (R,S)-4-propionylamino-1-[2-phenylacetic acid-N(3,5-bis-trifluoromethyl-benzyl)-amide]-piperidine were obtained as a white solid.

Yield: 64%. Mp: 189–191° C. FAB-MS: (M+H)$^+$=516.4.

Example 33

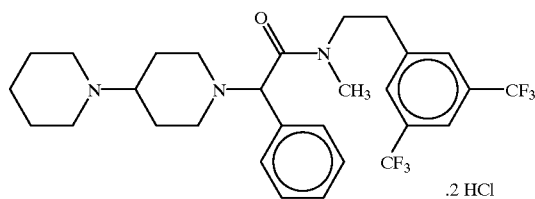

Mp: >240° C.; FAB-MS: (M+H)$^+$=556.4

0.3 g of the compound according to Example 25 were converted into the corresponding base by treatment with KHCO$_3$ and dried. The resulting product was dissolved in 5 ml of anhydrous THF, 34 mg of NaH (60% in oil) were added and the mixture was stirred for 1.5 hours at room temperature. Then 0.1 g of methyliodide were added and the mixture was stirred overnight. The reaction mixture was mixed with 2 ml of THF/water (1:1) then with 25 ml of water and extracted 3 times with ether. The combined ether extracts were dried over Na$_2$SO$_4$ and evaporated down in vacuo, thereby obtained 170 mg of the desired compound in the form of a free base (oil). This was converted into the dihydrochloride by the addition of an excess of ethereal HCl, the dihydrochloride being obtained in the form of yellow crystals.

Yield: 113 mg (36%).

The other compounds of the invention may be prepared analogously, e.g. as follows:

Example 3

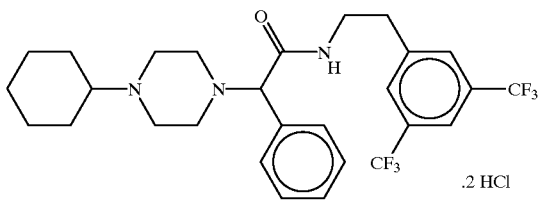

Mp: 235–238° C. FAB-MS: (M+H)$^+$=542.2.

Example 4

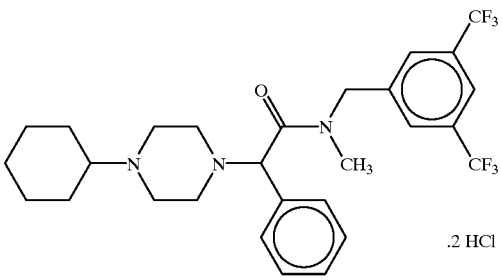

Mp: >240° C. (Decomp.). FAB-MS: (M+H)$^+$=542.3.

Example 5
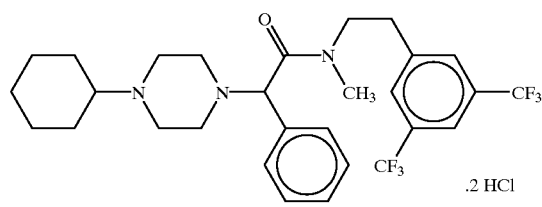
Mp: 158–164° C.; FAB-MS: (M+H)⁺=556.4.
Example 6
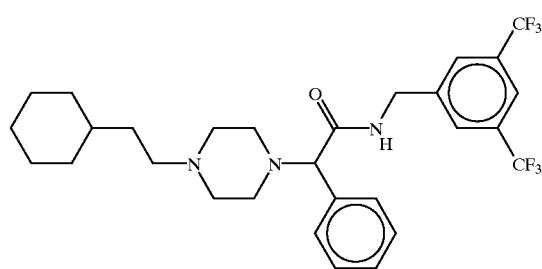
Mp: 97–99° C.; FAB-MS: (M+H)⁺=556.3.
Example 7
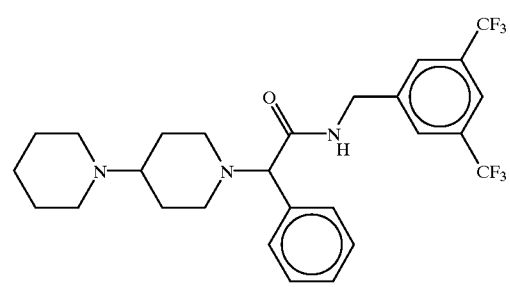
Mp: >240° (Decomp.); FAB-MS: (M+H)⁺=528.4.
Example 8
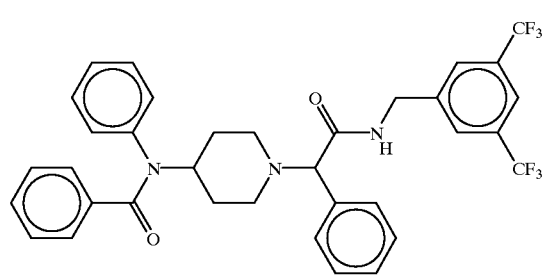
Mp: 102–105° C.; FAB-MS: (M+H)⁺=640.3.
Example 9
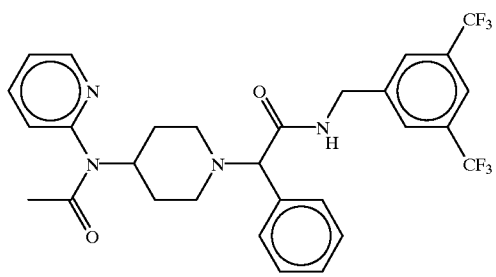
Mp: 141–149° C.; FAB-MS: (M+H)⁺=579.2.
Example 10
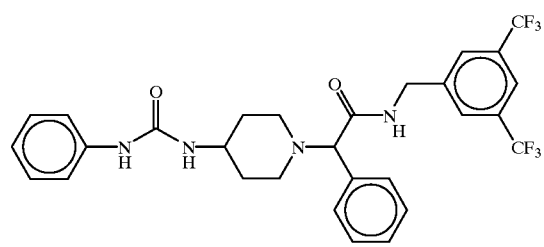
Mp: 218–223° C.; FAB-MS: (M+H)⁺=579.3.
Example 11
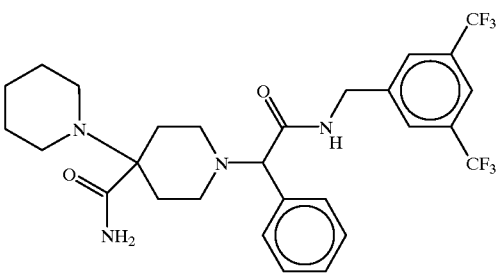
Mp: >220° (Decomp.) FAB-MS (M+H)⁺=571.3
Example 12
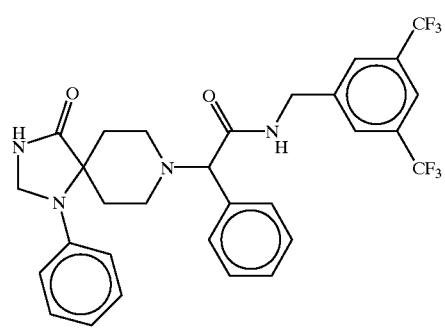
Mp: 205–210° C.; FAB-MS: (M+H)⁺=591.3.

Example 13
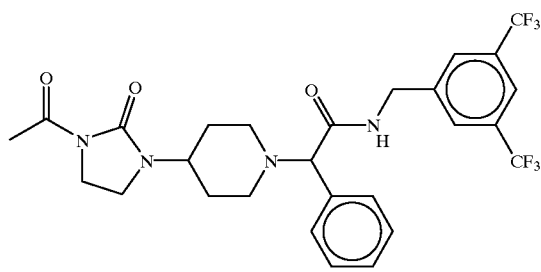
MP: 87–95° C.; FAB-MS: (M+H)⁺=571.2
Example 14
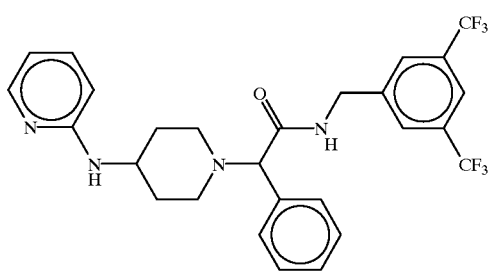
Mp: 164–166° C.; FAB-MS: (M+H)⁺=537.3.
Example 15
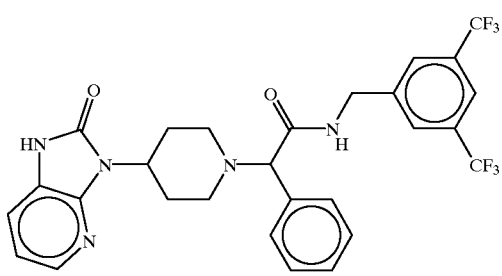
Mp: 208–210° C.; FAB-MS: (M+H)⁺=578.3.
Example 16
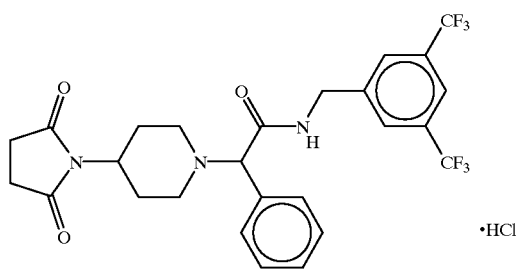
•HCl
Mp: 110–115° C.; FAB-MS: (M+H)⁺=542.3.
Example 17
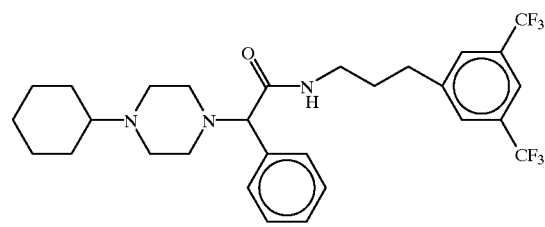
Mp: 118–123° C.; FAB-MS: (M+H)⁺=556.3
Example 18
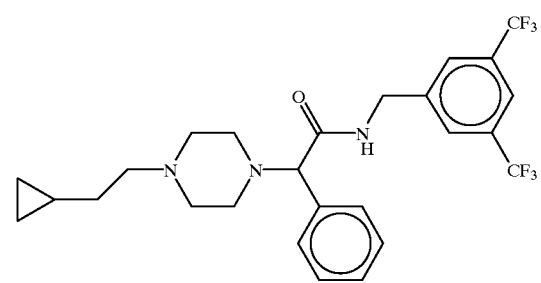
Mp: 134–136° C.; FAB-MS: (M+H)⁺=514.3
Example 19
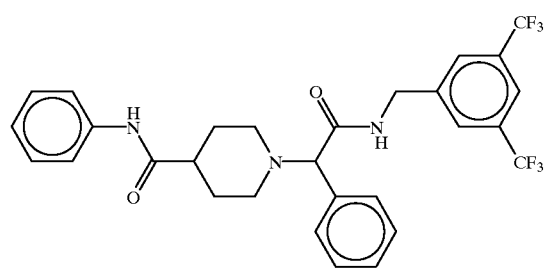
Mp: >240° (Decomp.): FAB-MS: (M+H)⁺=564
Example 20
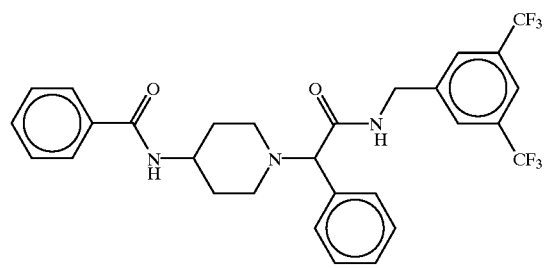
Mp: 180–185° C.; FAB-MS: (M+H)⁺=564.3

Example 21
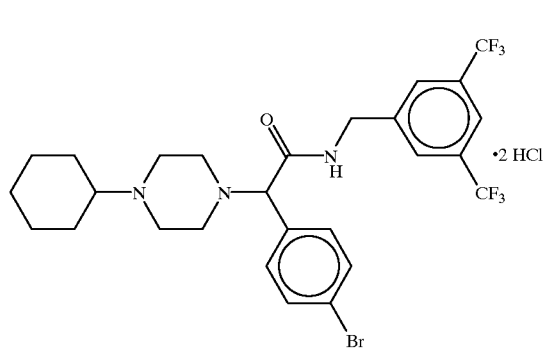
Mp: 228–232° C.; FAB-MS: (M+H)$^+$=606/608
Example 22
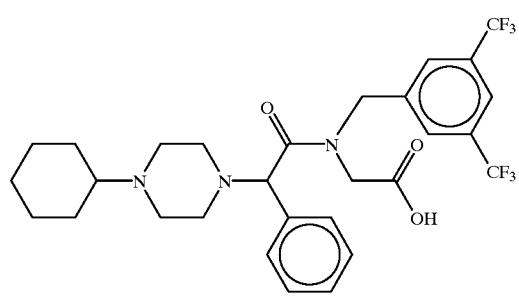
Mp: 70–73° C.; FAB-MS: (M+H)$^+$=586
Example 23
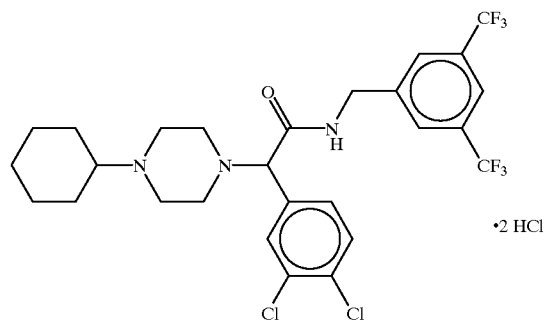
Mp: 248–254° C.; FAB-MS: (M+H)$^+$=596/598/600
Example 24
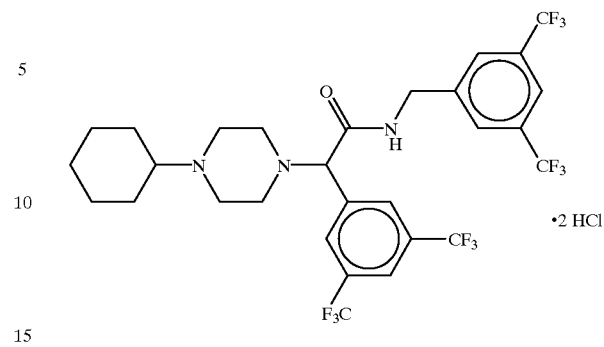
Mp: 210° C.; FAB-MS: (M+H)$^+$=664.1
Example 25
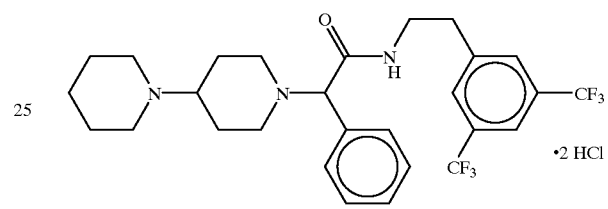
Mp: 192–199° C.; FAB-MS: (M+H)$^+$=542.3
Example 26
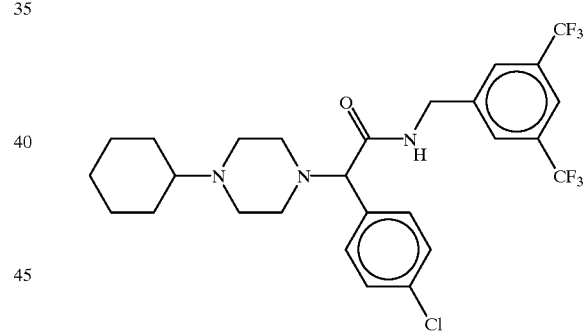
Mp: 112–118° C.; FAB-MS: (M+H)$^+$=562/564
Example 27
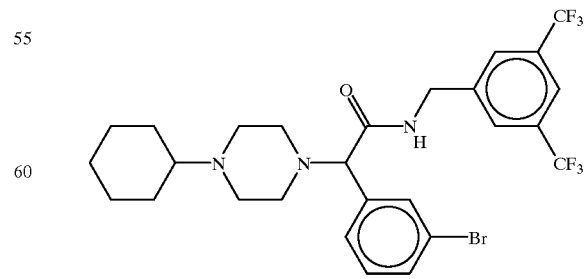
Mp: 124–127° C.; FAB-MS: (M+H)$^+$=606/608

Example 28
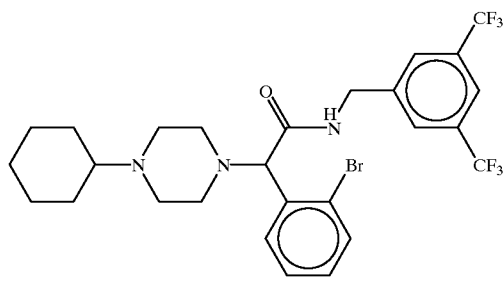
Mp: 118–120° C.; FAB-MS: (M+H)⁺=606/608
Example 29
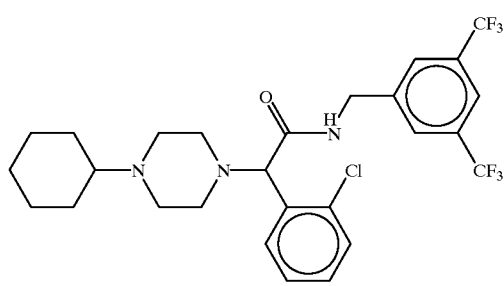
Mp: 120–122° C.; FAB-MS: (M+H)⁺=562/564
Example 30
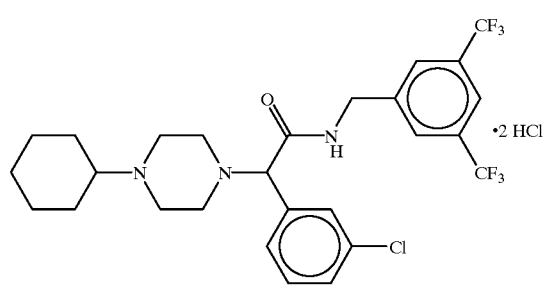
Mp: >240° C.; FAB-MS: (M+H)⁺=562/564
Example 31
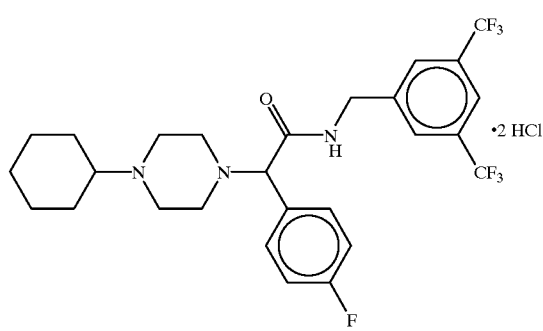
Mp: >240° C.; FAB-MS: (M+H)⁺=546.3
Example 32
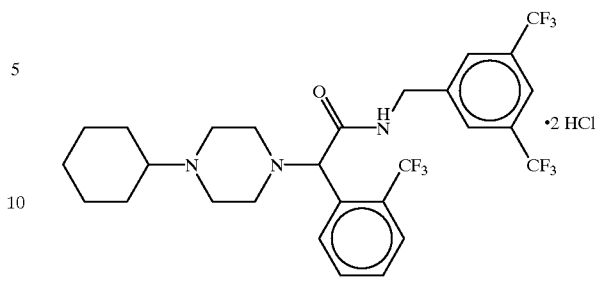
Mp: 125–130° C. (Decomp.); FAB-MS: (M+H)⁺=610.4
Example 33
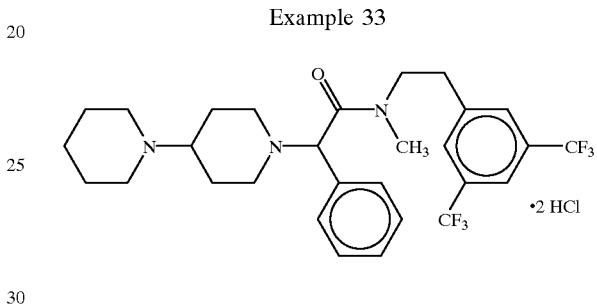
Mp: >240° C.; FAB-MS: (M+H)⁺=556.4
Example 34
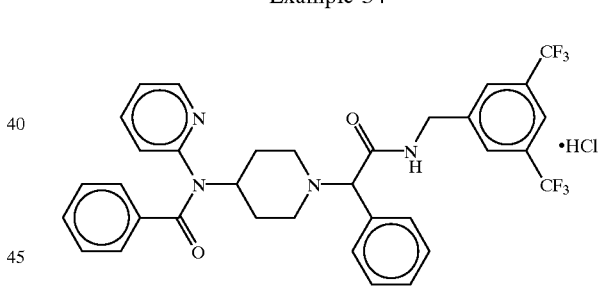
Mp: 145–151° C.; FAB-MS: (M+H)⁺=641.3
Example 35
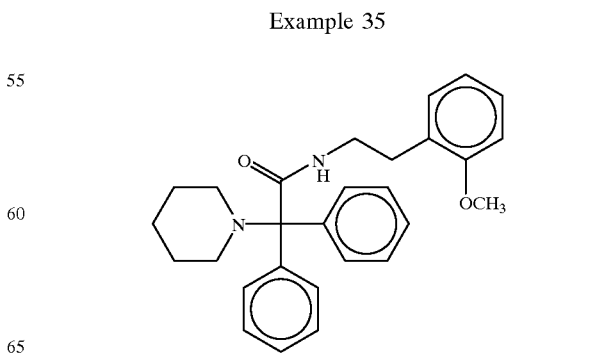

Example 36
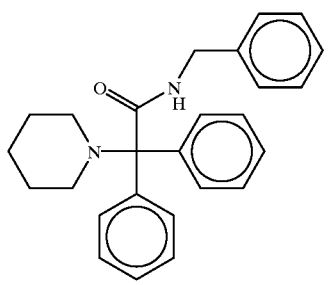
Mp: 175–176.5° C.
Example 37
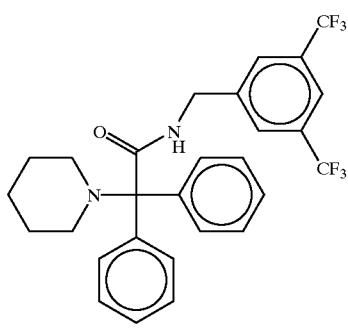
Mp: 157–158° C.
Example 38
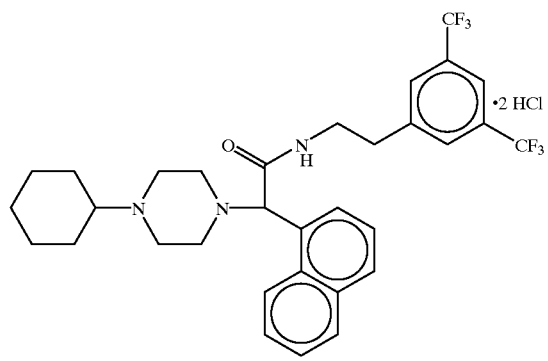
Mp: 155–172° C. FAB-MS: (M+H)⁺=592.2
Example 39
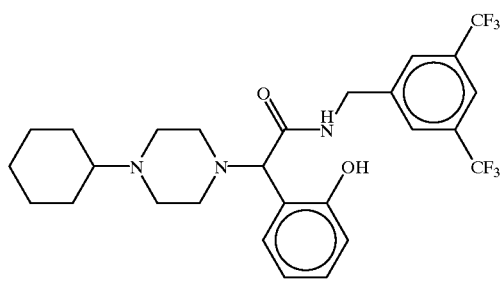
Example 40
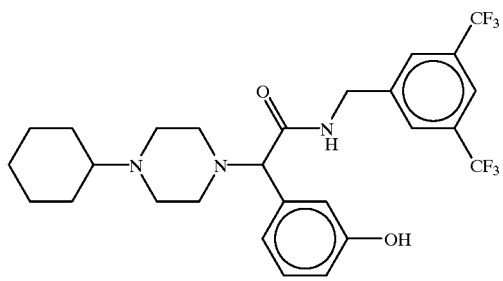
Example 41
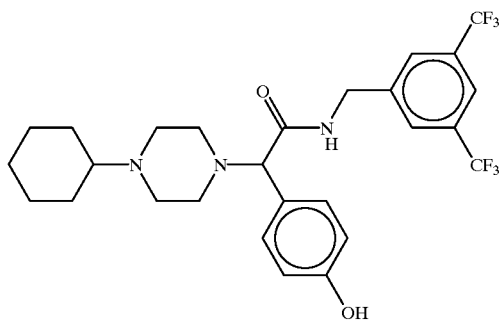
Example 42
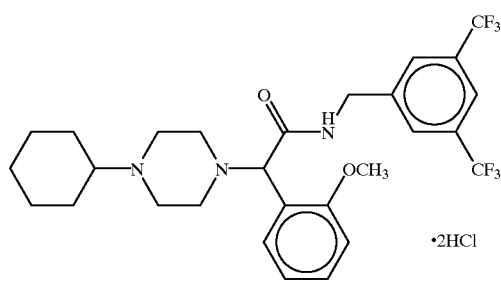
Mp: 142–150° C.
FAB-MS: (M+H)⁺=558.2

Example 43
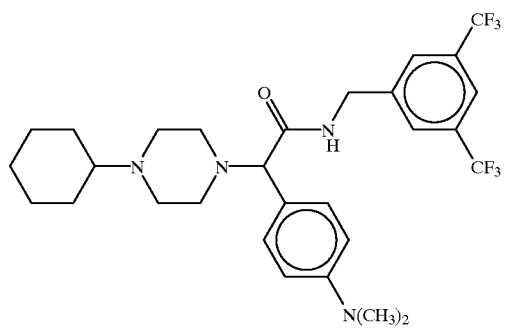
Example 44
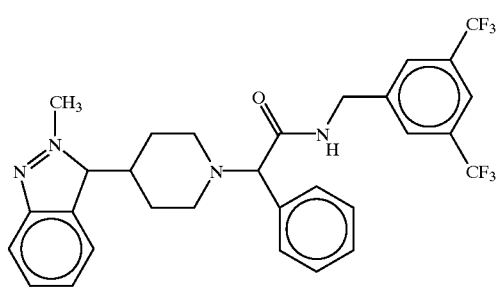
Mp: 107–111° C.; FAB-MS: (M+H)⁺=575.6
Example 45
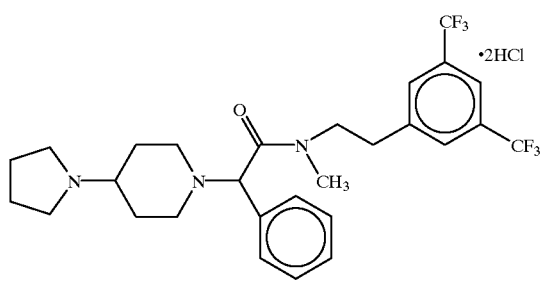
M.p: >230° C.
Example 46
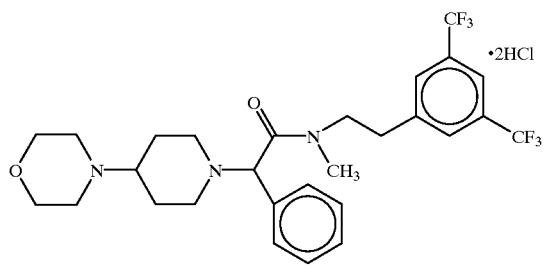
M.p: >230° C.
Example 47
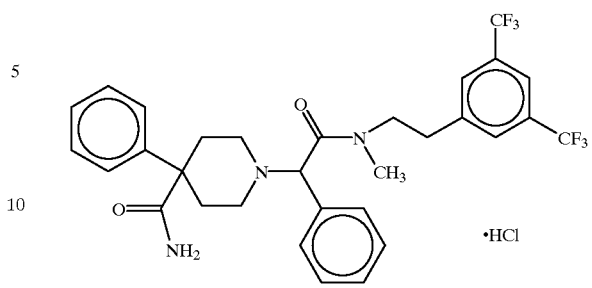
M.p: 127–137° C.
FAB-MS: (M+H)⁺=592
Example 48
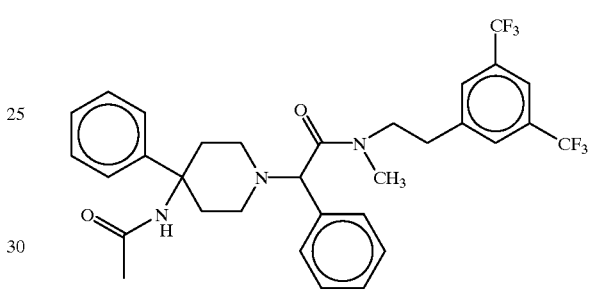
Example 49
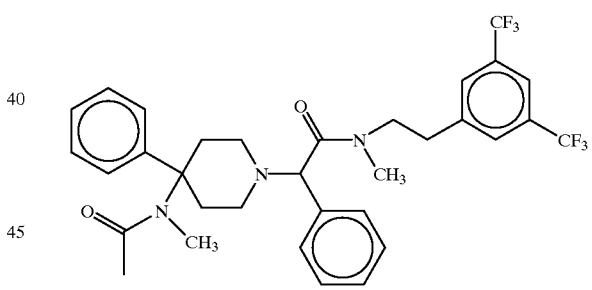
Example 50
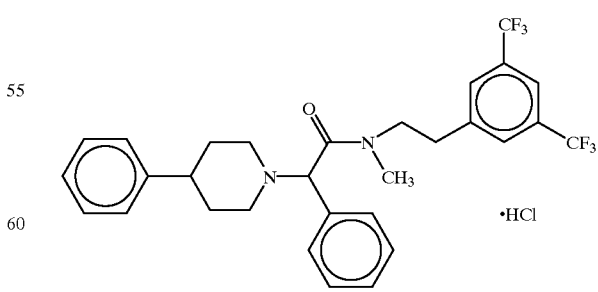
M.p. 106–110° C.
FAB-MS: (M+H)⁺=549

Example 51
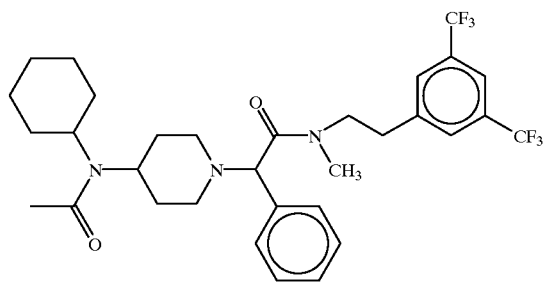
Example 52
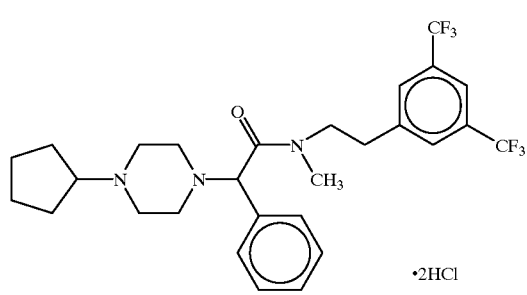
·2HCl
Mp: 133–143° C.
FAB-MS: (M+H)+=542.3
Example 53
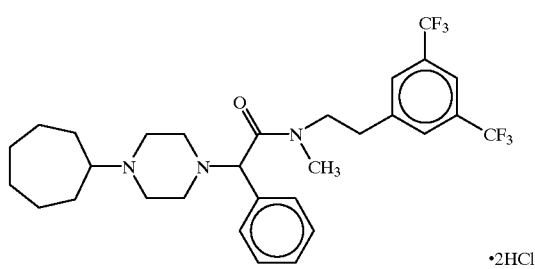
·2HCl
M.p. 110–120° C.
FAB-MS: (M+H)+=570.4
Example 54
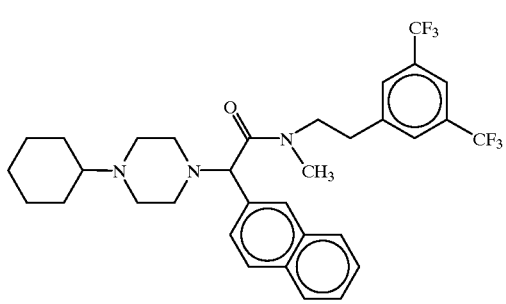
Example 55
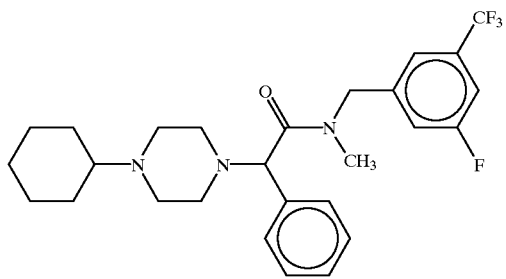
Example 56
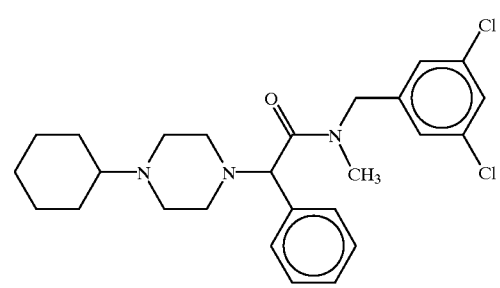
Example 57
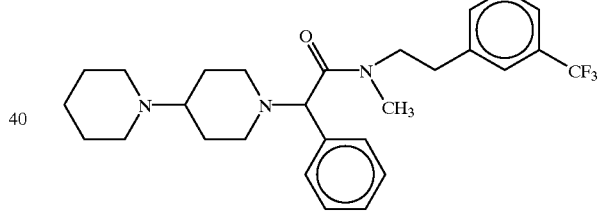
Example 58
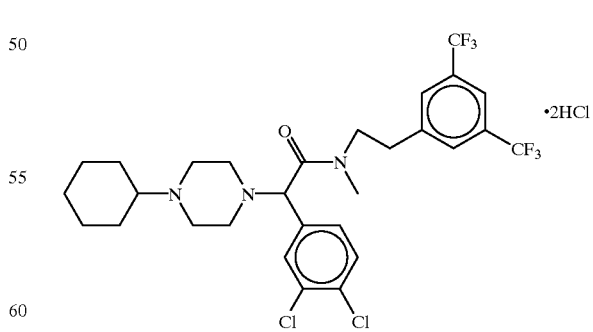
·2HCl
Mp: 212–216° C. (Decomp.)
FAB-MS: (M+H)+=624.3/626.3/628.3

Example 59
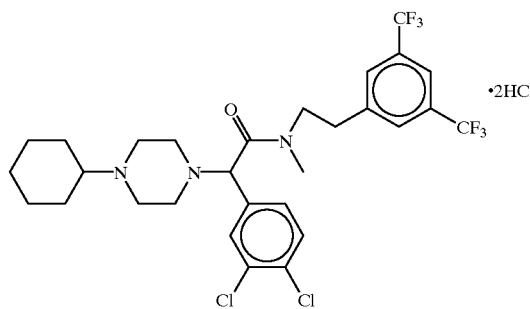
Mp: 244–246° C. (Decomp.)
FAB-MS: (M+H)⁺=624.1/626.2/628
Example 60
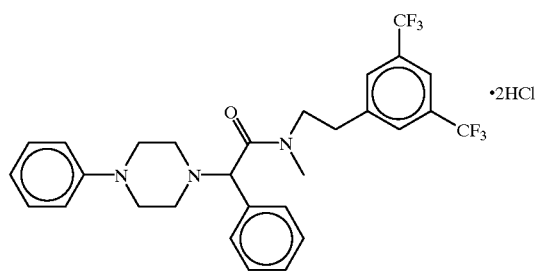
Mp: 113–123° C.
FAB-MS: (M+H)⁺=550.3
Example 61
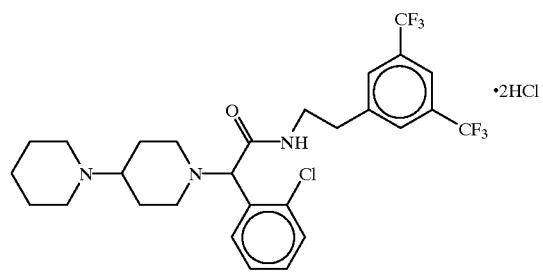
Mp: 195–205° C.
Example 62
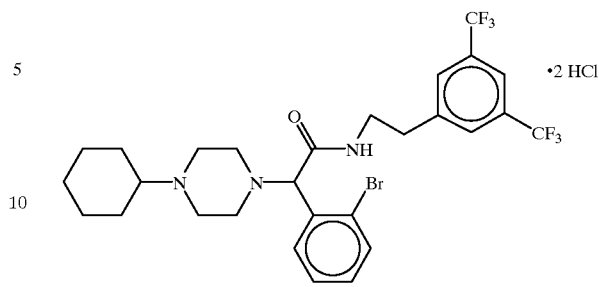
Mp: 210–218° C.
FAB-MS: (M+H)⁺=620/622
Example 63
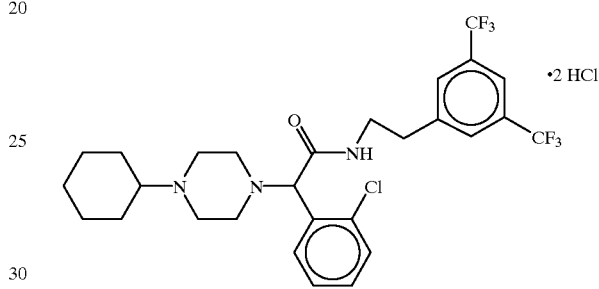
Mp: 215–224° C.
FAB-MS: (M+H)⁺=576/578
Example 64
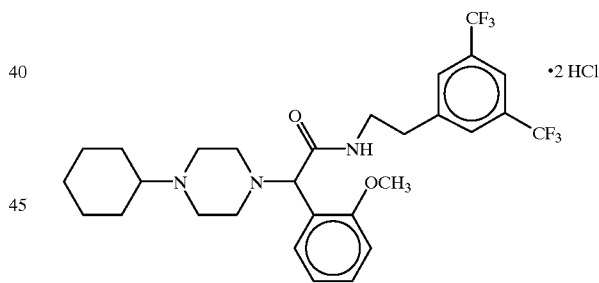
Mp: 85–92° C.
FAB-MS: (M+H)⁺=572.5
Example 65
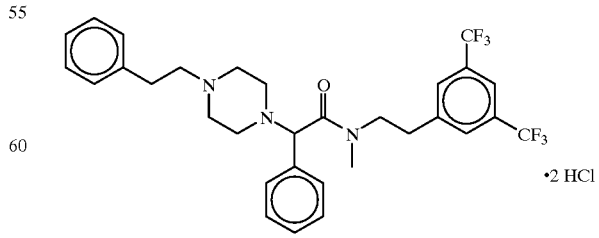
Mp: 148–156° C.
FAB-MS: (M+H)⁺=578.4

Example 66
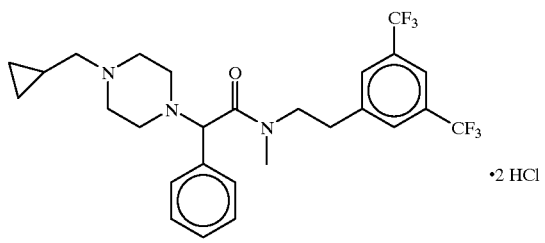
•2 HCl
Mp: 113–117° C. (decomp.)
FAB-MS: (M+H)⁺=528.5
Example 67
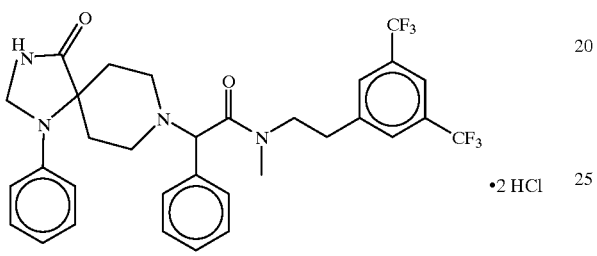
•2 HCl
Mp: 265–268° C. (decomp.)
FAB-MS: (M+H)⁺=619.3
Example 68
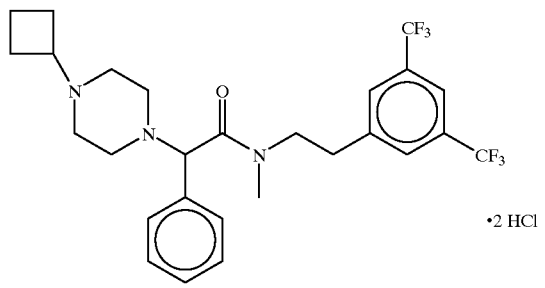
•2 HCl
Mp: 236–238° C. (decomp.)
FAB-MS: (M+H)⁺=528.3
Example 69
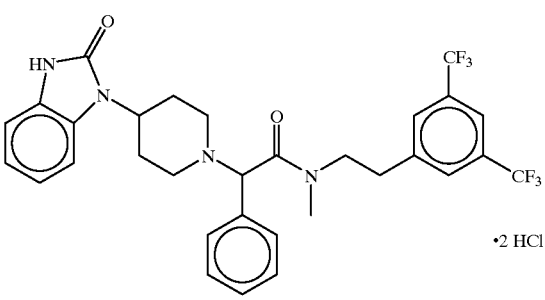
•2 HCl
Mp: 177–187° C. (Decomp.)
FAB-MS: (M+H)⁺=605.3
Example 70
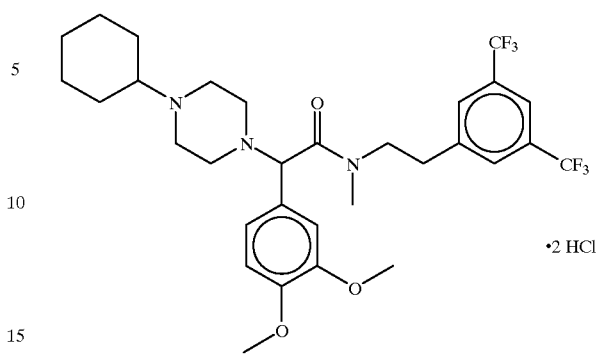
•2 HCl
Mp: 123–133° C. (decomp.)
FAB-MS: (M+H)⁺=616.3
Example 71
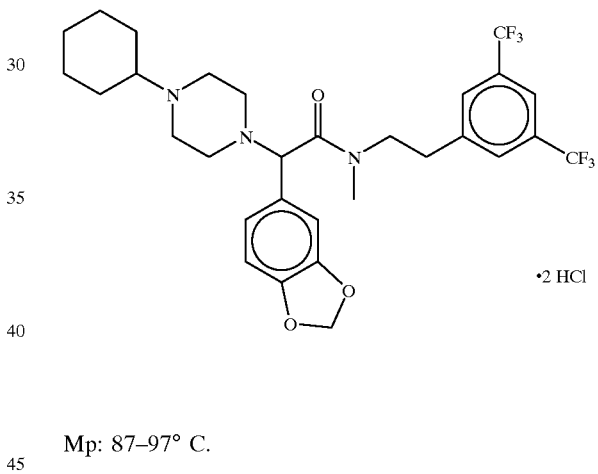
•2 HCl
Mp: 87–97° C.
FAB-MS: (M+H)⁺=600.2
Example 72
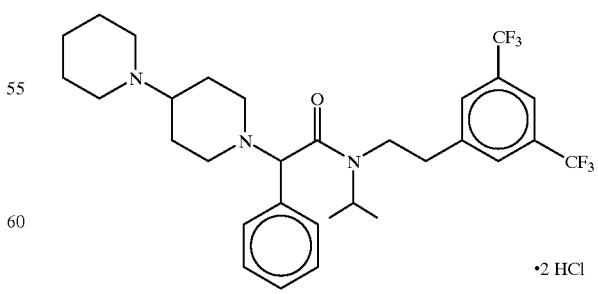
•2 HCl
Mp: >230° C.

Example 73

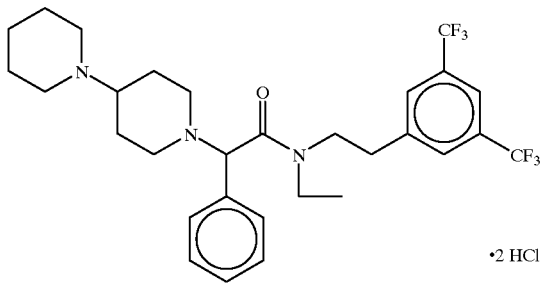

•2 HCl

Mp: >230° C.

Example 74

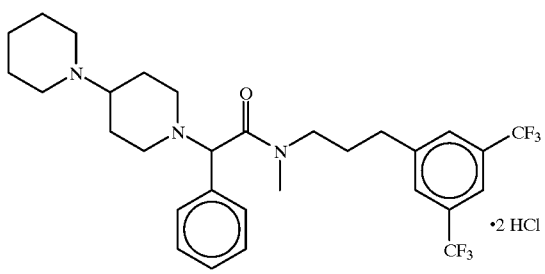

•2 HCl

Mp: >230° C.

Example 75

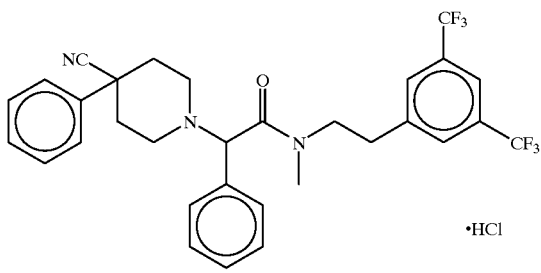

•HCl

Mp: 91–98° C.
FAB-MS: (M+H)⁺=574.4

Example 76

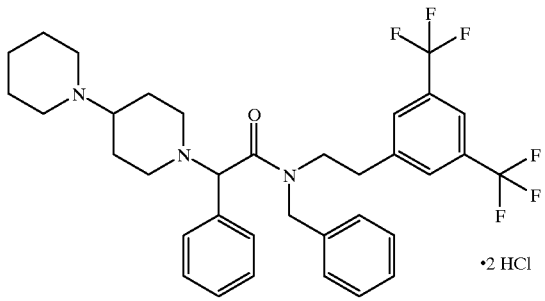

•2 HCl

Mp: 234–236° C.

Example 77

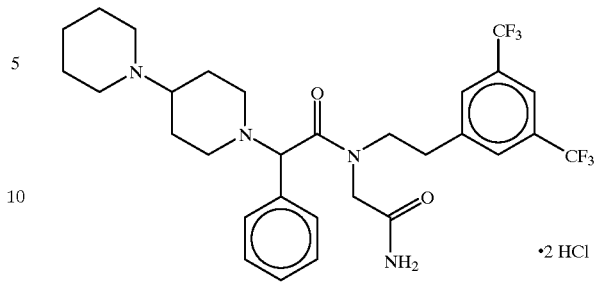

•2 HCl

Mp: 195–198° C.

Example 78

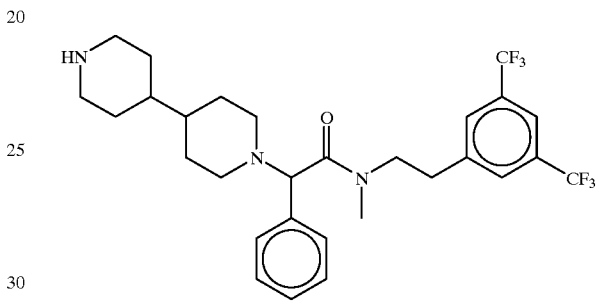

| Pharmaceutical Preparations: | |
|---|---|
| Injectable solution | |
| 200 mg | of active substance* |
| 1.2 mg | of monopotassium dihydrogen phospate = KH$_2$PO$_4$ ) |
| 0.2 mg | of disodium hydrogen phosphate = ) (buffer) NaH$_2$PO$_4$ . 2H$_2$O ) |
| 94 mg or | of sodium chloride ) ) (isotonic) |
| 520 mg | of glucose ) |
| 4 mg | of albumin (protease protection) |
| q.s. | sodium hydroxide solution ) |
| q.s. | hydrochloric acid ) to adjust the pH to pH 6 |
| sufficient water to make a 10 ml solution for injection | |
| Injectable solution | |
| 200 mg | of active substance* |
| 94 mg or | of sodium chloride |
| 520 mg | of glucose |
| 4 mg | of albumin |
| q.s. | sodium hydroxide solution ) |
| q.s. | hydrochloric acid ) to adjust the pH to pH 9 |
| sufficient water to make a 10 ml solution for injections | |
| Lyophilisate | |
| 200 mg | of active substance* |
| 520 mg | of mannitol (isotonic/structural component) |
| 4 mg | of albumin |
| Solvent 1 for lyophilisate | |
| 10 ml | of water for injections |
| Solvent 2 for lyophilisate | |
| 20 mg | of Polysorbate ® 80 = Tween ® 80 (surfactant) |
| 10 ml | of water for injections |

| Pharmaceutical Preparations: |
|---|
| * Active substance: compound according to the invention, e.g. that of Examples 1 to 78. |
| Dosage for humans weighing 67 kg: 1 to 500 mg |

We claim:

1. A compound of the following formula:

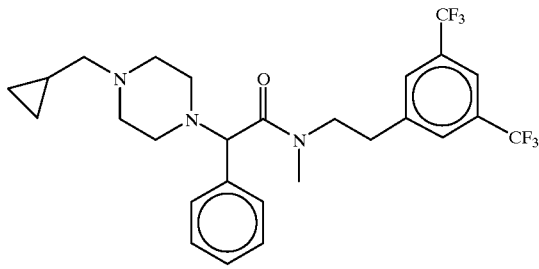

wherein said compound is a racemate or an enantiomer, or a pharmaceutically acceptable salt thereof.

2. The compound of claim 1, which is an enantiomer.

3. The compound of claim 1, which is a racemate.

4. The compound of claim 1 in the form of the bis hydrochloride salt.

5. A process for preparing the compound of claim 1, comprising the steps of:
   (a) reacting 1-cyclopropylmethyl-4-(2-phenylacetic acid)-piperazine, or an acid halide or alkyl ester thereof, with 3,5-bis-(trifluoromethyl)-phenethylamine;
   (b) reacting the product of step (a) with a methylhalide; and
   (c) isolating the product of step (b) as a free compound or as a pharmaceutically acceptable salt thereof.

6. A pharmaceutical composition, comprising the compound of claim 1 and a pharmaceutically acceptable carrier.

7. The pharmaceutical composition of claim 6 which is in the form of a solution, suspension or emulsion.

8. The pharmaceutical composition of claim 6, wherein said carrier is a polylactide, polyglycolide or polyhydroxybutyric acid.

9. The pharmaceutical composition of claim 6, which is an orally administrable pharmaceutical composition.

10. A method for the treatment of a neurokinin-mediated disease in an animal subject, comprising administering to said animal subject in need of such treatment an effective amount of the compound of claim 1.

11. The method of claim 10, wherein said neurokinin-mediated disease is selected from the group consisting of collagenosis, dysfunction of the urinary tract, hemorrhoids, nausea and vomiting, and pain.

12. The method of claim 10, wherein said neurokinin-mediated disease is an inflammatory disease of the respiratory tract, an allergic disease of the respiratory tract, an eye disease, a skin disease, a disease of the gastrointestinal tract, a disease of the joints, or a disease of the central nervous system.

13. The method of claim 10, wherein said neurokinin-mediated disease is an inflammatory or allergic disease of the respiratory tract selected from the group consisting of asthma, chronic bronchitis, emphysema, rhinitis and coughs.

14. The method of claim 10, wherein said neurokinin-mediated disease is an eye disease selected from the group consisting of conjunctivitis and iritis.

15. The method of claim 10, wherein said neurokinin-mediated disease is a skin disease selected from the group consisting of eczema, urticaria, psoriasis, sunburn, insect bites and stings, neurodermititis, itching, and postherpetic pain.

16. The method of claim 10, wherein said neurokinin-mediated disease is a disease of the gastrointestinal tract selected from the group consisting of gastric and duodenal ulcers, ulcerative colitis, Crohn's disease, irritable bowel and Hirschsprung's disease.

17. The method of claim 10, wherein said neurokinin-mediated disease is a disease of the joints selected from the group consisting of rheumatoid arthritis, reactive arthritis and Reiter syndrome.

18. The method of claim 10, wherein said neurokinin-mediated disease is a disease of the central nervous system selected from the group consisting of dementia, schizophrenia, psychosis, depression, headaches and epilepsy.

19. The method of claim 18, wherein said headache is a migraine headache or a tension headache.

20. The method of claim 10, wherein the method for said administering is orally administering.

21. The compound of claim 2, wherein said enantiomer is an R-enantiomer.

22. The compound of claim 2, wherein said enantiomer is an S-enantiomer.

* * * * *